United States Patent
Kim et al.

(10) Patent No.: US 8,426,577 B2
(45) Date of Patent: Apr. 23, 2013

(54) PROMOTER AND A PRODUCTION METHOD FOR L-LYSINE USING THE SAME

(75) Inventors: Chul Ha Kim, Seoul (KR); Jong Soo Choi, Seoul (KR); Sang Jo Lim, Incheon (KR); Hyung Joon Kim, Seoul (KR); Jun Ok Moon, Seoul (KR); Gey Hang Jeon, Seoul (KR); Jin Suk Sung, Yongin-si (KR)

(73) Assignee: CJ Cheiljedang Corporation, Seoul (KR)

( * ) Notice: Subject to any disclaimer, the term of this patent is extended or adjusted under 35 U.S.C. 154(b) by 127 days.

(21) Appl. No.: 12/864,731

(22) PCT Filed: Jan. 23, 2009

(86) PCT No.: PCT/KR2009/000381
§ 371 (c)(1),
(2), (4) Date: Jul. 27, 2010

(87) PCT Pub. No.: WO2009/096689
PCT Pub. Date: Aug. 6, 2009

(65) Prior Publication Data
US 2010/0317067 A1    Dec. 16, 2010

(30) Foreign Application Priority Data
Jan. 28, 2008   (KR) .................... 10-2008-0008620

(51) Int. Cl.
*C07H 21/04* (2006.01)
*C12P 13/08* (2006.01)
*C12N 1/12* (2006.01)

(52) U.S. Cl.
USPC ................ 536/24.1; 435/115; 435/252.1

(58) Field of Classification Search .................. None
See application file for complete search history.

(56) References Cited

U.S. PATENT DOCUMENTS

| | | |
|---|---|---|
| 6,221,636 B1 | 4/2001 | Hayakawa et al. ............ 435/115 |
| 6,746,855 B2 | 6/2004 | Kreutzer et al. ............... 435/115 |
| 2008/0014618 A1* | 1/2008 | Bathe et al. ..................... 435/115 |

FOREIGN PATENT DOCUMENTS

| | | |
|---|---|---|
| KR | 1997-043035 | 7/1997 |
| KR | 10-0397322 | 8/2003 |
| WO | WO 2007/141111 A2 | 12/2007 |

OTHER PUBLICATIONS

Cahyanto et al., "Regulation of aspartokinase, aspartate semialdehyde dehydrogenase, dihydrodipicolinate synthase and dihydrodipicolinate reductase in *Lactobacillus plantarum*," *Microbiology*, 152: 105-112, 2006.

Cremer et al., "Control of the Lysine Biosynthesis Sequence in *Corynebacterium glutamicum* as Analyzed by Overexpression of the Individual Corresponding Genes," *Applied and Environmental Microbiology*, 57 (6): 1746-1752, 1991.

Follettie et al., "Gene Structure and Expression of the *Corynebacterium flavum* N13 ask-asd Operon," *Journal of Bacteriology*, 175 (13): 4096-4103, 1993.

International Search Report, mailed Aug. 31, 2009, for PCT/KR2009/000381, 4 pages.

Kalinowski et al., "Aspartokinase genes *lysC*α and *lysC*β overlap and are adjacent to the aspartate β-semialdehyde dehydrogenase gene *asd* in *Corynebacterium glutamicum*," *Mol. Gen. Genet.*, 224: 317-324, 1990.

\* cited by examiner

*Primary Examiner* — Alexander Kim
(74) *Attorney, Agent, or Firm* — SEED IP Law Group PLLC

(57) ABSTRACT

Disclosed are a nucleic acid molecule of *Corynebacterium glutamicum* origin, having an improved promoter activity, which is operably linked to operon encoding aspartate kinase and aspartate semialdehyde dehydrogense, a vector containing the same, a transformant transformed with the vector, and a method for the production of L-lysine using the transformant.

10 Claims, 1 Drawing Sheet

PROMOTER AND A PRODUCTION METHOD FOR L-LYSINE USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_408USPCa$_{13}$ SEQUENCE_LISTING.txt. The text file is approximately 4 KB, was created on Dec. 17, 2012, and is being submitted electronically via EFS-Web. The text file of the Sequence Listing contains no new matter.

TECHNICAL FIELD

The present invention relates to an improved promoter and a method for producing L-lysine using the same. More particularly, the present invention relates to a nucleic acid molecule of *Corynebacterium glutamicum* origin, showing improved promoter activity, which is operably linked to operon encoding aspartate kinase and aspartate semialdehyde dehydrogenase, a vector containing the Nucleic acid molecule, a transformant with the vector introduced thereinto, and a method for producing L-lysine using the transformant.

BACKGROUND ART

Coryneform bacteria are traditionally industrial microorganisms which are most widely used for the production of a variety of chemical materials useful in the animal feed, medicine and food industries, including amino acids, such as L-lysine, L-threonine, L-arginine, L-threonine and glutamic acid, and nucleic acid-related materials. These microorganisms are Gram-positive and require biotin for their growth. They are divided by snapping and their poor ability to degrade the metabolites they produce can be advantageously utilized. Representative examples of coryneform bacteria include *Corynebacterium* genus, such as *Corynebacterium glutamicum*, *Brevibacterium* genus, such as *Brevibacterium flavum*, *Athrobacter* spp. and *Microbacterium* spp. etc.

L-lysine is a commercially important L-amino acid which is used as a feed additive in animal nutrition thanks to its ability to help the body to absorb other amino acids thus improving the quality of the feedstuff. For the body, L-lysine is used as an ingredient of an injection solution, and also finds applications in the pharmaceutical field. Therefore, the industrial production of L-lysine is economically important industrial process.

The production yield of lysine is correlated with enzyme activity on the biosynthesis pathway which can be typically enhanced by amplifying one or more genes on the biosynthesis pathway of lysine or by employing a modified promoter for the genes. *Corynebacterium* strains with lysine biosynthesis-associated genes enhanced therein and the production of L-lysine using the same are well known. For example, U.S. Pat. No. 6,746,855 discloses a process for the production of L-lysine by fermenting an L-lysine producing *corynebacteria* with enhanced lysE gene (lysine export carrier gene), in which additionally genes selected from the group consisting of a dapA gene, an lysC gene, a pyc gene and a dapB gene are enhanced. U.S. Pat. No. 6,221,636 discloses *corynebacteria* transformed with a recombinant DNA comprising a Nucleotide sequence coding for an aspartokinase in which feedback inhibition by L-lysine and L-threonine is substantially desensitized and a Nucleotide sequence coding for a diaminopimelate decarboxylase.

For the development of coryneform bacteria into variants capable of producing target products at high titers, a genetic or metabolic engineering technique by which genes involved in the metabolism can be selectively controlled is needed. To this end, it is important to modify a promoter activity, a regulatory DNA region which provides a secure initial binding site for RNA polymerase to control the transcription of regulated genes.

However, none of the coryneform bacteria which are improved in the activity of lysC-asd operon which plays a critical role in the lysine biosynthesis pathway, with an enhanced promoter have been disclosed thus far.

DISCLOSURE

Technical Problem

Leading to the present invention, intensive and thorough research into the production of L-lysine, resulted in the finding that when being transformed with a lysC-asd operon promoter, modified at particular bases, on the genome of *corynebacterium*, a *corynebacterium* genus microorganism shows aspartate kinase and aspartate semialdehyde dehydrogenase activity improved over the endogenous activity.

Technical Solution

It is an object of the present invention to provide a nucleic acid molecule originating from *Corynebacterium glutamicum* which exhibits improved promoter activity.

It is another object of the present invention to provide a vector containing the nucleic acid molecule which exhibits improved promoter activity.

It is a further object of the present invention to provide a transformant with the vector anchored therein.

It is still a further object of the present invention to provide a method for producing L-lysine by fermenting the transformant.

Advantageous Effects

When being operably linked to a lysC-asd gene, the nucleic acid molecule originating from *Corynebacterium*, showing improved promoter activity, *C. glutamicum* in accordance with the present invention shows higher promoter activity than does the wild-type promoter, and thus can increase levels of aspartate kinase and aspartate semialdehyde dehydrogenase. Therefore, the lysine-producing strain transformed with the nucleic acid molecule can produce lysine at higher yield.

BEST MODE

Figure 1:
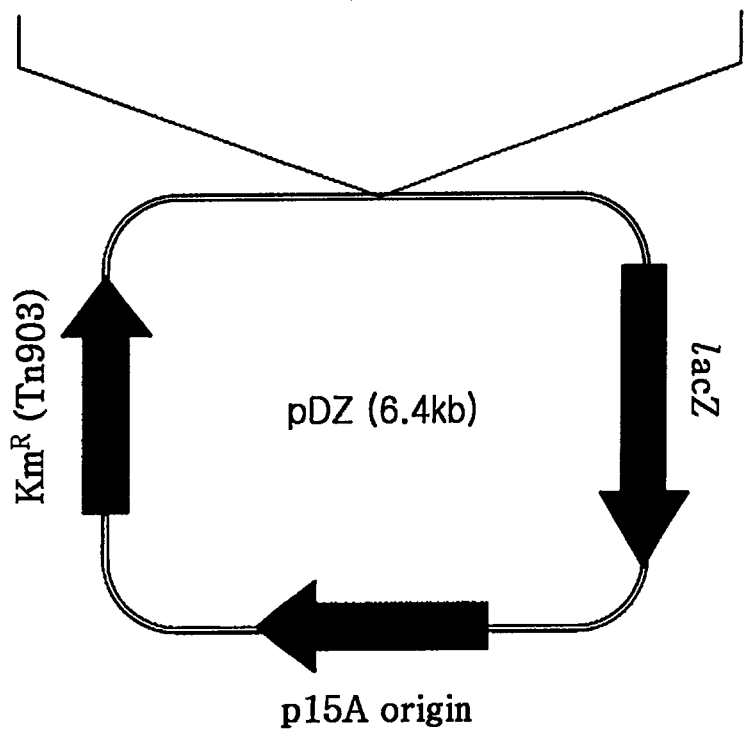
FIG. 1 is a diagram showing a genetic map of the vector pDZ for integration into a *corynebacterium* genome.

In accordance with an aspect thereof, the present invention pertains to a nucleic acid molecule of *Corynebacterium glutamicum* origin having a nucleotide sequence of SEQ ID NO. 2, which is operably linked to operon encoding aspartate kinase and aspartate semialdehyde dehydrogenase and exhibits improved promoter activity.

The term "promoter", as used herein, refers to a DNA region which contains an initial binding site for RNA polymerase and facilitates the transcription of a particular gene downstream thereof. That is, a promoter is an untranslated nucleotide sequence, upstream of a coding region, to which RNA polymerase binds to initiate the transcription of a gene, and is typically located near the genes it regulate, on the same strand and upstream (towards the 5' region of the sense strand).

The nucleic acid molecule of the present invention, originating from *Corynebacterium glutamicum*, having a promoter activity, is operably linked to operon encoding aspartate kinase and aspartate semialdehyde dehydrogenase. The lysC and asd genes, respectively encoding aspartate kinase and aspartate semialdehyde dehydrogenase, play an important role in the biosynthesis pathway of lysine in *Corynebacterium* spp.

In coryneform bacteria, a lysC gene is comprised of two overlapping genes, that is, lysC alpha and lysC beta, which are adjacent to the third open reading frame (ORFS) responsible for asd which is known to be expressed as a part of the lysC operon, with the initiation codon of asd starting at the position 24 by downstream of the end of the lysC ORF. The term "operon", as used herein, refers to a functional cluster of adjacent genes under the control of single regulatory signal, consisting of an operator, a promoter and a structural gene. In the present invention, lysC and asd genes belong to the lysC-asd operon and are under the control of the same promoter.

The term "operably linked", as used herein, is intended to refer to a linkage between the nucleotide sequence having a promoter activity according to the present invention and the promoter sequence in such a functional relationship that the promoter can serve to initiate and mediate the transcription of genes coding respectively for aspartate kinase and aspartate semialdehyde dehydrogenase. That is, when operably linked to a lysC-asd operon gene, the nucleotide sequence having a promoter activity in accordance with the present invention can control the transcription activity of the operon gene.

The nucleotide sequence having a promoter activity in accordance with the present invention, originating from a wild-type promoter of the lysC-asd operon of *Corynebacterium glutamicum*, is modified to guarantee an enzymatic activity superior to the endogenous activity. The endogenous activity means an activity of enzyme in the wile type coryneform bacteria. Modification for guaranteeing higher promoter activity can be achieved using techniques well known in the art, preferably by inducing a mutation on the nucleotide sequence of the promoter of the lysC-asd operon through deletion, insertion, non-conservative or conservative substitution or a combination thereof.

The nucleic acid molecule having a promoter activity in accordance with the present invention may be isolated or prepared using a standard biological technique. For example, PCR may be performed for isolation in the presence of proper primers. Alternatively, it may be synthesized with standard biological technique using an automated DNA synthesizer. In an embodiment, on the basis of a nucleotide sequence (SEQ ID NO. 1) containing a promoter region of a lysC-asd gene (NCBI gene ID: NCg10247) obtained from the data of the NIH GenBank, four primers (SEQ ID NOS. 3~6) were synthesized. In the presence of the primers, PCR was performed to give a promoter-containing Nucleic acid molecule which had modifications at particular base positions (SEQ ID NO. 2), with the genomic DNA of *Corynebacterium glutamicum* KFCC10881 serving as a template.

Preferably, the Nucleic acid molecule having a *Corynebacterium glutamicum* promoter activity in accordance with the present invention is useful as a promoter for gene expression in prokaryotes, especially *E. coli* or coryneform bacteria. As used herein, the term "coryneform bacteria" refers to a microorganism belonging to the *Corynebacterium* genus or the *Brevibacterium* genus. Examples of coryneform bacteria useful in the present invention include, but are not limited to, *Corynebacterium glutamicum* ATCC13032, *Corynebacterium thermoaminogenes* FERM BP-1539, *Brevibacterium flavum* ATCC 14067, *Brevibacterium lactofermentum* ATCC 13869, and L-amino acid-producing mutants or strains originating therefrom, such as *Corynebacterium glutamicum* KFCC10881 and *Corynebacterium glutamicum* KFCC11001, with preference for *Corynebacterium glutamicum* KFCC 10881.

In accordance with another aspect thereof, the present invention pertains to a vector in which the Nucleic acid molecule having an improved promoter activity is located.

As used herein, the term "vector" refers to a DNA construct in which a gene of interest is operably linked to a regulatory element so that the gene can be expressed in a proper host which anchors the vector therein. The regulatory element includes a promoter for initiating transcription, an operator for controlling transcription, a sequence coding for an mRNA ribosome-binding site, and a sequence for controlling the termination of transcription and translation.

So long as it is replicable in hosts, any vector known in the art may be employed in the present invention, without particular limitations. For example, the vector useful in the present invention may be a plasmid, a phage particle, or simply a potential genomic insert, but the present invention is not limited thereby. A preferable vector is pACYC177 (New England Biolab, GenBank accession # X06402). After being transformed into a suitable host, the vector may be replicated or perform its function irrespective of the host genome or may be integrated into the genome itself.

In greater detail, when the vector according to the present invention is introduced into a host cell, the nucleic acid molecule having the promoter activity in the vector may undergo homologous recombination with a promoter region for an endogenous promoter of the lysC-asd operon on the host genome, resulting in the integration of the vector into the chromosome of the host cell. Therefore, the vector according to the present invention may further comprise a selection marker for indicating the insertion of the vector into the host chromosome. Adapted to indicate a cell transformed with the vector, that is, whether a gene of interest is inserted into the genome of the host cell, the selection marker may endow the cell with ability to show drug resistance, cytotoxic agent resistance, auxotrophy, or selectable phenotype expression such as the expression of a surface protein. In the presence of a selective agent, transformed cells may be selected because only the cells which express the selection marker rendering survive or show another phenotype. Preferably, the vector may comprise a lacZ gene as a selection marker.

Figure 2:
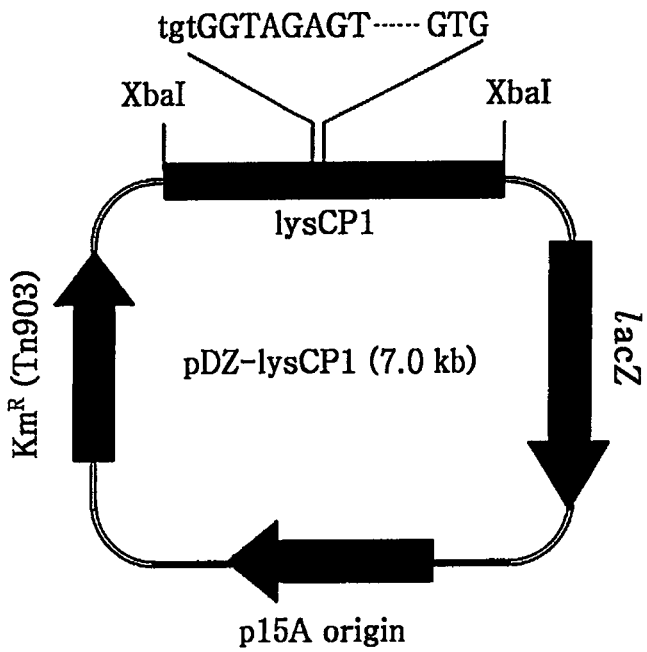
FIG. 2 is a diagram showing a genetic map of the vector pDZ-lysCP1 for promoter. The sequence "tgtGGTAGAGT" in FIG. 2 corresponds to nucleotides 300-310 of SEQ ID NO:2.

In an embodiment of the present invention, a vector is constructed to contain a modified ddh promoter improved in activity which can be substituted for the endogenous ddh promoter of *Corynebacterium glutamicum* through homologous recombination. To this end, first, the vector pACYC177 for *E. coli* cloning is digested with restriction enzymes and blunt ended with Klenow fragment. Separately, a nucleotide sequence comprising a lacZ gene and its promoter is amplified from the genomic DNA of *E. coli* K12W3110 through PCR. These two DNA fragments thus obtained are ligated to each to give a circular Nucleic acid molecule, followed by inserting an adaptor sequence containing multiple restriction enzyme sites therein into the circular Nucleic acid molecule to afford the vector pDZ for insertion into the chromosome of *Corynebacterium* (FIG. 1). Thereafter, a ddh gene promoter modified at particular bases to show high activity is inserted into the adaptor sequence of the pDZ vector to give the vector pDZ-lysCP1 comprising the nucleotide sequence of SEQ ID NO. 2 (FIG. 2).

In accordance with a further aspect thereof, the present invention pertains to a transformant with the vector anchored therein.

The term "transformation", as used herein, refers to the introduction of an exogenous DNA material into a host cell in which the exogenous DNA material is replicable as an element separated from or incorporated into the host genome. Resulting from the transformation of the vector into a host cell, the transformant anchors the vector in the form of a plasmid or as is incorporated into the chromosome of the host cell after the nucleotide sequence having a promoter activity undergoes homogenous recombination with an endogenous promoter of the lysC-asd operon on the genome of the host cell.

So long as it is used to introduce the vector of the present invention into a host cell, any technique may be employed in the present invention. Depending on a host cell, a suitable standard technique may be selected, for example, among electroporation, calcium phosphate ($CaPO_4$) precipitation, calcium chloride ($CaCl_2$) precipitation, microinjection, a polyethyleneglycol (PEG) technique, a DEAE-dextran technique, a cationic liposome technique, and a lithium acetate-DMSO technique.

It is useful to use a cell which is highly efficient in the uptake and expression of foreign DNA materials, and it can be applicable to all microorganism including prokaryote and eukaryote. Preferably, *E. coli* or coryneform bacteria may be used, and more preferable is

*Corynebacterium glutamicum* KFCC10881.

In the cells transformed with the vector of the present invention, the modified promoter of the lysC-asd operon having improved activity is substituted for the endogenous promoter through homologous recombination, potentiating the mRNA level of the lysC-asd operon gene. As a result, the transformant has higher aspartate kinase and aspartate semi-aldehyde dehydrogenase activity than dose the wild-type.

In an embodiment of the present invention, the vector pDZ-lysCP1 in which the promoter having a nucleotide sequence of SEQ ID NO. 2 in accordance with the present invention was transformed into Corynebacterium glutamicum KFCC10881 to give a transformant (KFCC10881- lysCP1), named CA01-0135, showing improved aspartate kinase and aspartate semialdehyde dehydrogenase activity. The transformant was then deposited according to the Budapest Treaty with the Korean Culture Center of Microorganisms (hereinafter referred to as "KCCM") as *Corynebacterium glutamicum* CA01-0135, under Accession Number KCCM10919P on Jan. 18, 2008. The KCCM depository is located at 361-221, Yurim B/D, Hongie-1-dong, Seodaemun-gu, SEOUL 120-091, Republic of Korea.

In accordance with a further aspect thereof, the present invention pertains to a method for the production of lysine comprising the fermentation of the transformant.

Compared to the wild-type, the transformant according to the present invention is improved in aspartate kinase and aspartate semialdehyde dehydrogenase activity. Because aspartate kinase and aspartate semialdehyde dehydrogenase are the most essential enzymes on the biosynthesis pathway of lysine, the fermentation of the transformant leads to the production of lysine at higher yield.

In the present invention, the fermentation of the transformant may be conducted using a well-known method, and conditions for the fermentation, including temperature, time, pH, etc. may be controlled properly. A detailed description is given of the fermentation in the following document [Chmiel; Bioprozesstechnik 1. Einfuhrung in die Bioverfahrenstechnik (Gustav Fischer Verlag, Stuttgart, 1991), and Storhas; Bioreaktoren and periphere Einrichtungen (Vieweg Verlag, Braunschweig/Wiesbaden, 1994)]. The fermentation may be achieved by batch cultivation, continuous cultivation or fed-batch cultivation. Preferably, a fed batch or repeated fed batch process is used in a continuous manner for the fermentation, but the present invention is not limited thereto.

For use in the fermentation, a medium must satisfy the requirement of the strain employed. Culture media suitable for use in culturing various microorganisms are well known in the art (e.g., "Manual of Methods for General Bacteriology" from American Society for Bacteriology (Washington D.C., USA, 1981)). Culture media may contain as carbon sources saccharides and carbohydrates (e.g., glucose, sucrose, lactose, fructose, maltose, molasse, starch and cellulose), lipids and fats (e.g., soybean oil, sunflower seed oil, peanut oil and coconut oil), fatty acids (e.g., palmitic acid, stearic acid, rinoleic acid), alcohols (e.g., glycerol and ethanol) and organic acids (e.g., acetic acid). These materials may be used in separation or in combination. As nitrogen sources, nitrogen-containing organic compounds (e.g., peptone, yeast extract, broth, malt extract, corn steep liquor, soybean meal and urea), or inorganic compounds (e.g., ammonium sulfate, ammonium chloride, ammonium phosphate, ammonium carbonate and ammonium nitrate) may be used in separation or in combination. Examples of phosphorus sources useful in the culture media include dipotassium hydrogen phosphate, potassium dihydrogen phosphate and corresponding sodium salts.

Also, culture media may contain metal salts essential to the growth of cells (e.g., magnesium sulfate or ferrous sulfate) and may be supplemented with essential nutrients for stimulating growth such as amino acids and vitamins. In addition, proper precursors may be added to the culture media. The nutrients or supplements may be added altogether once or in separation during fermentation.

The pH of the culture media may be adjusted with an alkaline compound (e.g., sodium hydroxide, potassium hydroxide or ammonia) or an acidic compound (e.g., phosphoric acid or sulfuric acid). The generation of foams in culture media may be restrained using an anti-foaming agent such as fatty acid polyglycol ester. The culture media may be kept under an aerobic condition by introducing oxygen or an oxygen-containing gas mixture thereinto. As to the culture temperature, it is typically between 20 and 45° C. and preferably between 25 and 40° C. The fermentation is continued until a maximal amount of L-amino acid is produced. In this regard, it may be accomplished within 10 to 160 hrs. After being produced, the L-lysine may be exported into the culture media or may remain within the cells.

Alternatively, the method for the production of lysine in accordance with the present invention may further comprise collecting the produced lysine. L-lysine can be isolated from culture media or cells using a well-known method. Examples of the collecting method useful in the present invention include filtration, anionic exchange chromatography, crystallization and HPLC, but are not limited thereto.

A better understanding of the present invention may be obtained through the following examples which are set forth to illustrate, but are not to be construed as limiting the present invention.

Mode for Invention

In the following examples, a recombinant vector was constructed to contain a promoter of the lysC-asd operon of *Corynebacterium glutamicum* which was modified to have improved activity. The recombinant vector was transformed into *Corynebacterium glutamicum* KFCC10881 in which the modified promoter was then incorporated into the genome of the cell by homologous recombination with the endogenous promoter, resulting in a novel strain capable of producing lysine at higher yield.

Artificially mutated from a *Corynebacterium glutamicum* wild-type strain (ATCC13032), *Corynebacterium glutamicum* KFCC10881 useful in the present invention was resistant to S-(2-aminoethyl) cysteine (hereinafter referred to as "AEC") and homoserine leaky (Korean Patent Nos. 0159812 and 0397322).

Example 1

Construction of Recombinant Vector Containing Improved Promoter (1) Construction of a Vector for Integration into Genome (pDZ)

In this example, pDZ, a vector to be integrated into *Corynebacterium* genome, was constructed on the basis of pACYC177 (New England Biolab, GenBank accession # X06402), a vector for use in *E. coli*.

After being treated with AcuI and BanI, the pACYC177 vector was blunt ended with a Klenow fragment. For the use as a selection marker, a lacZ gene originating from *E. coli* was prepared by amplifying a genomic DNA of *E. coli* K12 W3110 comprising the gene and its promoter through PCR, followed by treating the PCR product with T4 DNA polymerase and polynucleotide kinase to phosphorylate at 5' end and make the opposite ends blunt, respectively. The two DNA fragments thus obtained were ligated to each other to give a circular Nucleic acid molecule into which an artificially synthesized adaptor sequence containing a plurality of restriction enzyme sites was then inserted to afford the vector pDZ for insertion into the chromosome of *Corynebacterium*. In FIG. 1, the pDZ vector for integration into *Corynebacterium* chromosome is schematically illustrated.

(2) Construction of a Vector Containing an Improved Promoter for lysC-asd Operon In this example, a recombinant vector was constructed to contain an improved promoter of the lysC-asd operon of the lysine-producing strain *Corynebacterium glutamicum*.

On the basis of the data of the NIH GenBank, first, a nucleotide sequence (SEQ ID NO. 1) comprising a promoter region (NCBI ID No. NCg10247) of the lysC-asd gene was obtained. From this nucleotide sequence was prepared a DNA fragment which was mutated at particular base positions. Each modified promoter sequence was designed on the basis of a typical consensus promoter sequence found in microorganisms.

For use in the preparation of the modified promoter sequences, four primers (SEQ ID NOS. 3~6, Table 1) were synthesized based on the base sequences.

TABLE 1

| Primer | Nucleotide Sequence | SEQ ID NO. |
|---|---|---|
| lysC/PF | CCG GGG ATC CTC TAG ACC ATC TTT TGG GGT GCG GAG C | 3 |
| lysC/PR | GCA GGT CGA CTC TAG ACT CAA TAG CCA TGG CGA CGA G | 4 |
| lysC/P1F | AGT TTA TTG TGG TAG AGT TG | 5 |
| lysC/P1R | CAA CTC TAC CAC AAT AAA CT | 6 |
| lysC/P1mut | GAC ACA GTT TAT TGT | 7 |

A promoter sequence of the lysC-asd operon of *Corynebacterium glutamicum* was prepared by PCR using sets of the primers of Table 1 in the presence of PfuUltra™ High-Fildelity DNA Polymerase (Stratagene) with the genomic DNA of *Corynebacterium glutamicum* KFCC10881 serving as a template. PCR was performed with 30 cycles of denaturation at 96° C. for 30 sec, annealing at 53° C. for 30 sec and extension at 72° C. for 30 sec. As a result, the PCR product was 300 by long DNA fragment with the substitution portion located at one terminal region. lysCP1-1 was amplified with a set of the primers of SEQ ID NOS. 3 and 6, and lysCP1-2 with a set of the primers of SEQ ID NOS. 4 and 5. The PCR product was digested with XbaI, and cloned into pDZ using an In-fusion Cloning Kit (TAKARA) to afford the recombinant vector pDZ-lysCP1.

FIG. 2 is a map of the vector pDZ-lysCP1 containing the promoter sequence of SEQ ID NO.2 which is integrated into *Corynebacterium* genome.

Example 2

Introduction of the Recombinant Vector into *Corynebacterium glutamicum* Strain

In this example, the recombinant vector prepared above was introduced into the lysine-producing strain *Corynebacterium glutamicum* KFCC-10881, so that the modified ddh promoter sequence on the vector was integrated into the genome of the cell through homologous recombination with the endogenous promoter of the lysC-asd operon on the genome.

To this end, the recombinant vector pDZ-lysCP1 containing the DNA fragment corresponding to the modified promoter sequence was transformed into *Corynebacterium glutamicum* KFCC10881 using an electroporation method (based on Appl. Microbiol. Biotechnol. (1999) 52:541-545), followed by selecting on a selection medium containing kanamycin in an amount of 25 mg/L the transformants in which the modified promoter was integrated into the genome through homologous recombination with the endogenous promoter.

Success in the insertion of the vector into the genome was identified by the appearance of a blue color on the plate containing X-gal (5-bromo-4-chloro-3-indolyl-β-D-galactoside). Single crossovers with the vector incorporated into the genome thereof were cultured in a nutrient broth with agitation (30° C., 8 hrs) after which the culture was diluted to a concentration of from $10^{-4}$ to $10^{-10}$ before being spread over plates containing X-gal. While most of the colonies grown on the plates appeared blue, only a low proportion of the colonies remained white. The white colonies were selected as double-crossover colonies which anchored the promoter of the lysC-asd operon which was mutated at particular base positions. For confirmation, the selected strains were examined for base substitution by PCR and base sequenced. The strain transformed with pDZ-lysCP1 was examined for base substitution in the promoter, using a set of primers of SEQ ID NOS. 4 and 7, by PCR and base sequencing.

The lysine-producing strain *Corynebacterium glutamicum* KFCC10881-lysCP1 in which the promoter of lysC-asd operon mutated at particular base positions was integrated into the genome thereof was finally confirmed through double crossover.

Example 3

Assay of the lysC-asd Promoter-Improved Strain for Aspartate kinase Activity

The mother strain *Corynebacterium glutamicum* KFCC10881 and the L-lysine-producing strain *Corynebacterium glutamicum* KFCC10881-lysCP1 finally prepared in Example 2 were cultured, and proteins were isolated from the cultures and assayed for aspartate kinase activity, as follows.

Each of the cultures grown to the logarithm phase was inoculated into 50 mL of the following seed medium to give an $OD_{600}$ of 0.3, and then incubated until the optical density at 600 nm reached about 15. After being collected through centrifugation (5,000 rpm, 15 min), cell mass was washed twice with 0.1% Tris HCl (pH 8.0) and suspended in the same buffer to an optical absorbance at 610 nm of turbidity 160. Cells were disrupted for 6 min in a glass beater with glass beads added at 1.25 g/1.5 ml of the suspension. After centrifugation (15,000 rpm, 20 min), the supernatant was quantitatively measured for protein content by a Bradford method (Bradford, M. M 1976. Anal. Biochem. 72:248-254) and used as a crude protein solution for measuring the activity of aspartate kinase.

In order to quantify the activity of aspartate kinase, about 0.05 mL of the crude protein solution was mixed with a reaction solution containing 0.1 M Tris HCl (pH 8.0), 0.01M $MgCl_2$, 0.6 M Hydroxylamine HCl (pH 7.0), 4 mM ATP, and 0.2 M Aspartate and allowed to react at 30° C. for 30 min, followed by adding a Stop solution (10% $FeCl_2$, 3.3% TCA, 0.7 N HCl) to terminate the reaction. After centrifugation, the supernatant thus obtained was measured for absorbance at 540 nm. The activity of aspartate kinase was defined as nmoles of the aspartate hydroxamate generated by 1 mg of protein per min and expressed in unit (U).

*Corynebacterium glutamicum* KFCC10881-lysCP1 was observed to have a aspartate kinase activity 5.08-fold higher than that of the mother strain KFCC10881 (Table 2).

TABLE 2

| Strain | Aspartate kinase (U) | Folds |
| --- | --- | --- |
| KFCC10881 | 13.5 | 1.00 |
| KFCC10881-lysCP1 | 68.6 | 5.08 |

Seed medium (pH 7.0)

Raw sugar 20 g, Peptone 10 g, Yeast extract 5 g, Urea 1.5 g, $KH_2PO_4$ 4 g, $K_2HPO_4$ 8 g, $MgSO_4$ $7H_2O$ 0.5 g, Biotin 100 µg, Thiamine HCl 1000 µg, Calcium pantothenate 2000 µg, Nicotine amide 2000 µg (per liter of distilled water)

Example 4

Lysine Production in the lysC-asd Promoter-Improved Strain

The mother strain *Corynebacterium glutamicum* KFCC10881 and the L-lysine-producing strain *Corynebacterium glutamicum* KFCC10881-lysCP1 prepared in Example 2 were fermented to produce L-lysine, as follows.

The mother strain *Corynebacterium glutamicum* KFCC10881 and KFCC10881-lysCP1 were inoculated into 250 mL corner-baffle flasks, each containing 25 mL of the following seed medium, and cultured at 30° C. for 20 hrs with shaking at 200 rpm. To 24 mL of the following production medium in a 250 mL corner-baffle flask was added 1 mL of the seed culture, followed by incubation at 30° C. for 120 hrs with shaking (200 rpm).

After the completion of culture, HPLC analysis was performed to determine the amounts of the L-lysine produced by the strains. The concentrations of L-lysine in the cultures of *Corynebacterium glutamicum* KFCC10881 and KFCC10881-lysCP1 are summarized in Table 3, below.

TABLE 3

| | Lysine (g/l) | | |
| --- | --- | --- | --- |
| Strain | Batch 1 | Batch 2 | Batch 3 |
| KFCC10881 | 43 | 42.5 | 42.7 |
| KFCC10881-lysCP1 | 45.3 | 45.2 | 45.7 |

Seed medium (pH 7.0)

Raw sugar 20 g, Peptone 10 g, Yeast extract 5 g, Urea 1.5 g, $KH_2PO_4$ 4 g, $K_2HPO_4$ 8 g, $MgSO_4$ $7H_2O$ 0.5 g, Biotin 100 µg, Thiamine HCl 1000 µg, Calcium pantothenate 2000 µg, Nicotine amide 2000 µg (per liter of distilled water)

*Production medium (pH 7.0)

Glucose 100 g, $(NH_4)_2SO_4$ 40 g, Soybean protein 2.5 g, Corn steep solids 5 g, Urea 3 g, $KH_2PO_4$ 1 g, $MgSO_4$ $7H_2O$ 0.5 g, Biotin 100 µg, Thiamine chloride 1000 µg, Calcium pantothenate 2000 µg, Nicotine amide 3000 µg, $CaCO_3$ 30 g (per liter of distilled water)

As seen in Table 3, *Corynebacterium glutamicum* KFCC-lysCP1 with about 5-fold improved aspartate kinase activity was found to increase in lysine productivity by about 5%, compared with the mother strain KFCC10881.

INDUSTRIAL APPLICABILITY

Having higher promoter activity than that of the wild-type, as described hitherto, the nucleic acid molecule of *Corynebacterium glutamicum* origin according to the present invention can enhance aspartate kinase and aspartate semialdehyde dehydrogenase activity, thus increasing the biosynthesis efficiency of lysine. Consequently, the strain which anchors the improved promoter can produce L-lysine, an industrially important amino acid, at high yield.

The invention claimed is:

1. An isolated nucleic acid molecule comprising nucleotides 1-353 of SEQ ID NO:2, having promoter activity for expression.

2. A vector comprising the nucleic acid molecule of claim 1.

3. The vector according to claim 2, which is pDZ-lysCP1 having a genetic map of FIG. 2.

4. A transformant transformed with the vector of claim 2, wherein the transformant is a prokaryote.

5. The transformant according to claim 4, wherein the prokaryote is a *Corynebacterium* or *Brevibacterium*.

6. The transformant according to claim 4, which is named CA01-0135, and deposited with Accession No. KCCM10919P.

7. The transformant according to claim 4, wherein the nucleic acid molecule of claim 1 having promoter activity is incorporated into a genome of the transformant through homologous recombination.

8. The transformant according to claim 4, harboring the nucleic acid molecule of claim 1 in a plasmid.

9. A method for producing lysine, comprising fermenting the transformant of claim 4.

10. The method according to claim 9, further comprising collecting the lysine generated during the fermentation.

* * * * *

SEQUENCE LISTING

<160> NUMBER OF SEQ ID NOS: 7

<210> SEQ ID NO 1
<211> LENGTH: 611
<212> TYPE: DNA
<213> ORGANISM: Corynebacterium glutamicum

```
<220> FEATURE:
<221> NAME/KEY: gene
<222> LOCATION: (1)..(611)
<223> OTHER INFORMATION: lysC promoter and some portion of lysC-asd gene

<400> SEQUENCE: 1
ccatcttttg gggtgcggag cgcgatccgg tgtctgacca cggtgcccca tgcgattgtt      60
aatgccgatg ctagggcgaa aagcacggcg agcagattgc tttgcacttg attcagggta     120
gttgactaaa gagttgctcg cgaagtagca cctgtcactt ttgtctcaaa tattaaatcg     180
aatatcaata tatggtctgt ttattggaac gcgtcccagt ggctgagacg catccgctaa     240
agccccagga accctgtgca gaaagaaaac actcctctgg ctaggtagac acagtttata     300
aaggtagagt tgagcgggta actgtcagca cgtagatcga aaggtgcaca aaggtggccc     360
tggtcgtaca gaaatatggc ggttcctcgc ttgagagtgc ggaacgcatt agaaacgtcg     420
ctgaacggat cgttgccacc aagaaggctg gaaatgatgt cgtggttgtc tgctccgcaa     480
tgggagacac cacggatgaa cttctagaac ttgcagcggc agtgaatccc gttccgccag     540
ctcgtgaaat ggatatgctc ctgactgctg gtgagcgtat ttctaacgct ctcgtcgcca     600
tggctattga g                                                         611

<210> SEQ ID NO 2
<211> LENGTH: 611
<212> TYPE: DNA
<213> ORGANISM: Corynebacterium glutamicum
<220> FEATURE:
<221> NAME/KEY: gene
<222> LOCATION: (1)..(611)
<223> OTHER INFORMATION: lysCP1 promoter and some portion of lysC-asd
      gene

<400> SEQUENCE: 2
ccatcttttg gggtgcggag cgcgatccgg tgtctgacca cggtgcccca tgcgattgtt      60
aatgccgatg ctagggcgaa aagcacggcg agcagattgc tttgcacttg attcagggta     120
gttgactaaa gagttgctcg cgaagtagca cctgtcactt ttgtctcaaa tattaaatcg     180
aatatcaata tatggtctgt ttattggaac gcgtcccagt ggctgagacg catccgctaa     240
agccccagga accctgtgca gaaagaaaac actcctctgg ctaggtagac acagtttatt     300
gtggtagagt tgagcgggta actgtcagca cgtagatcga aaggtgcaca aaggtggccc     360
tggtcgtaca gaaatatggc ggttcctcgc ttgagagtgc ggaacgcatt agaaacgtcg     420
ctgaacggat cgttgccacc aagaaggctg gaaatgatgt cgtggttgtc tgctccgcaa     480
tgggagacac cacggatgaa cttctagaac ttgcagcggc agtgaatccc gttccgccag     540
ctcgtgaaat ggatatgctc ctgactgctg gtgagcgtat ttctaacgct ctcgtcgcca     600
tggctattga g                                                         611

<210> SEQ ID NO 3
<211> LENGTH: 37
<212> TYPE: DNA
<213> ORGANISM: Artificial Sequence
<220> FEATURE:
<223> OTHER INFORMATION: primer lysC/PF

<400> SEQUENCE: 3
ccggggatcc tctagaccat cttttggggt gcggagc                              37
```

```
<210> SEQ ID NO 4
<211> LENGTH: 37
<212> TYPE: DNA
<213> ORGANISM: Artificial Sequence
<220> FEATURE:
<223> OTHER INFORMATION: primer lysC/PR

<400> SEQUENCE: 4
gcaggtcgac tctagactca atagccatgg cgacgag                              37

<210> SEQ ID NO 5
<211> LENGTH: 20
<212> TYPE: DNA
<213> ORGANISM: Artificial Sequence
<220> FEATURE:
<223> OTHER INFORMATION: primer lysC/P1F

<400> SEQUENCE: 5
agtttattgt ggtagagttg                                                  20

<210> SEQ ID NO 6
<211> LENGTH: 20
<212> TYPE: DNA
<213> ORGANISM: Artificial Sequence
<220> FEATURE:
<223> OTHER INFORMATION: primer lysC/P1R

<400> SEQUENCE: 6
caactctacc acaataaact                                                  20

<210> SEQ ID NO 7
<211> LENGTH: 15
<212> TYPE: DNA
<213> ORGANISM: Artificial Sequence
<220> FEATURE:
<223> OTHER INFORMATION: primer lysC/P1mut

<400> SEQUENCE: 7
gacacagttt attgt                                                       15
```